United States Patent [19]

Boone et al.

[11] Patent Number: 4,782,702
[45] Date of Patent: Nov. 8, 1988

[54] ULTRASONIC TESTING SYSTEM WITH VARIABLE ANGLE TRANSDUCER MOUNT

[75] Inventors: Bruce T. Boone, Cobb County; Steven Nafziger, Dekalb County; Thomas A. Rak; John A. McMennamy, both of Cobb County, all of Ga.

[73] Assignee: Movats Incorporated, Marietta, Ga.

[21] Appl. No.: 60,747

[22] Filed: Jun. 10, 1987

[51] Int. Cl.⁴ .............................................. G01B 17/00
[52] U.S. Cl. ...................................... 73/597; 73/629; 137/554; 367/104
[58] Field of Search ...................... 73/597, 622, 432.1, 73/866.5, 593, 620, 621, 627, 629; 367/104, 99; 137/554; 116/277; 33/1 P

[56] References Cited
U.S. PATENT DOCUMENTS
3,937,067  2/1976  Flambard et al. .................... 73/597

Primary Examiner—Stewart J. Levy
Assistant Examiner—Lawrence G. Fess
Attorney, Agent, or Firm—Louis T. Isaf

[57] ABSTRACT

An apparatus and method for achieving variable observations angles by a single transducer rotationally and pivotally mounted with a housing; and for utilizing the variable angle transducer to detect and trace and distance of unseen objects within a casing from the transducer by moving the transducer within its housing which is held stationary against the casing; and for determining the angle of observation between the transducer and the observed object; and thereby accurately determining the relative position and orientation of the object within the casing.

6 Claims, 3 Drawing Sheets

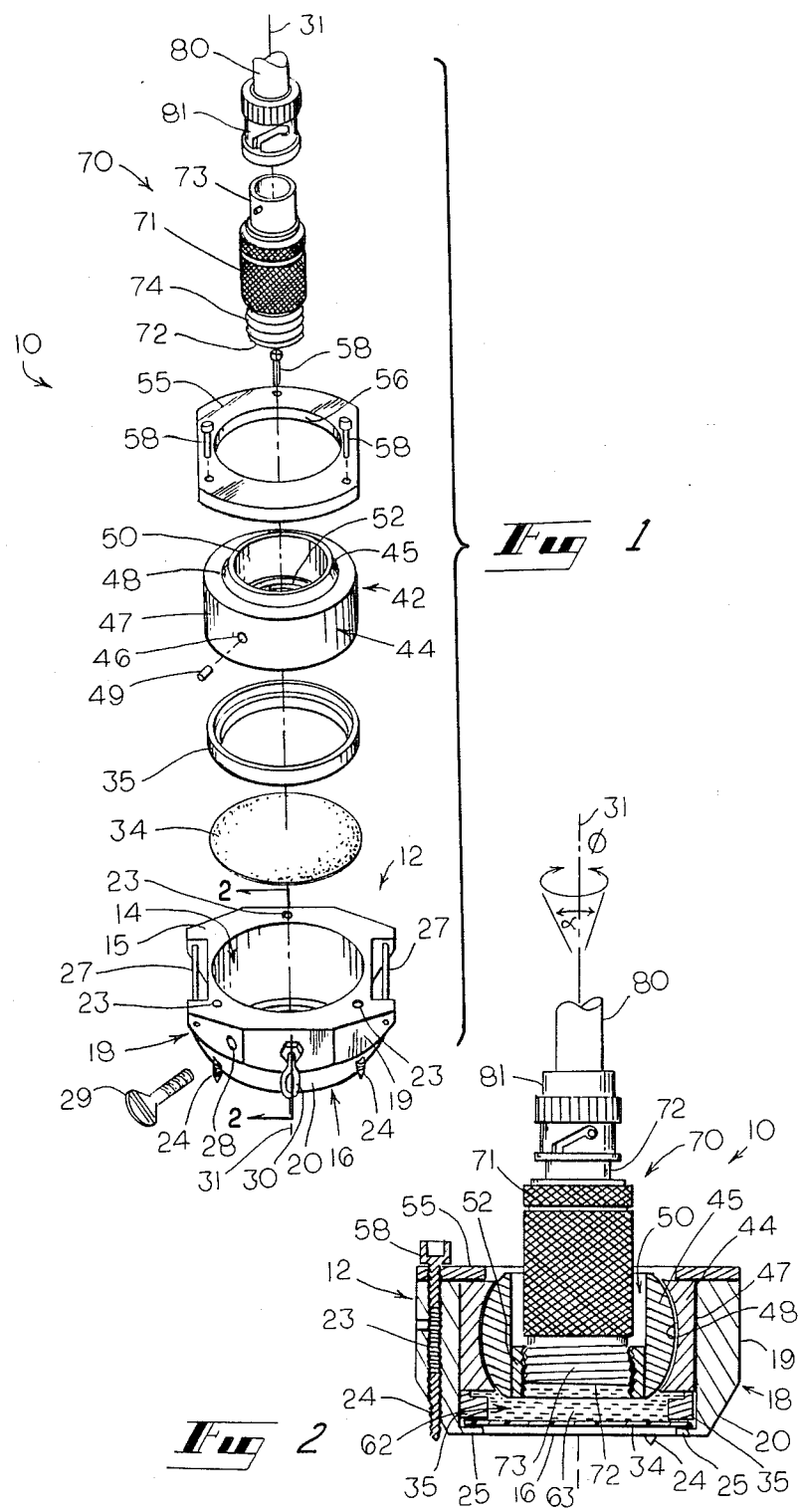

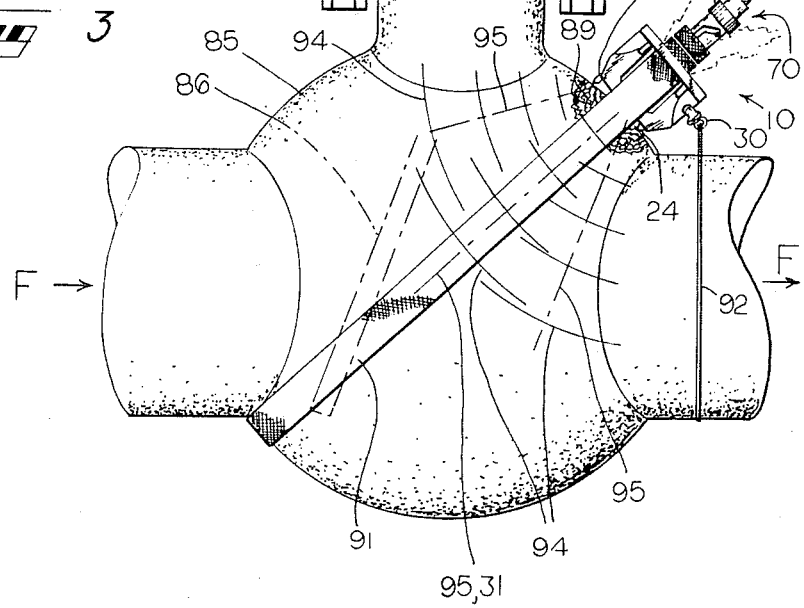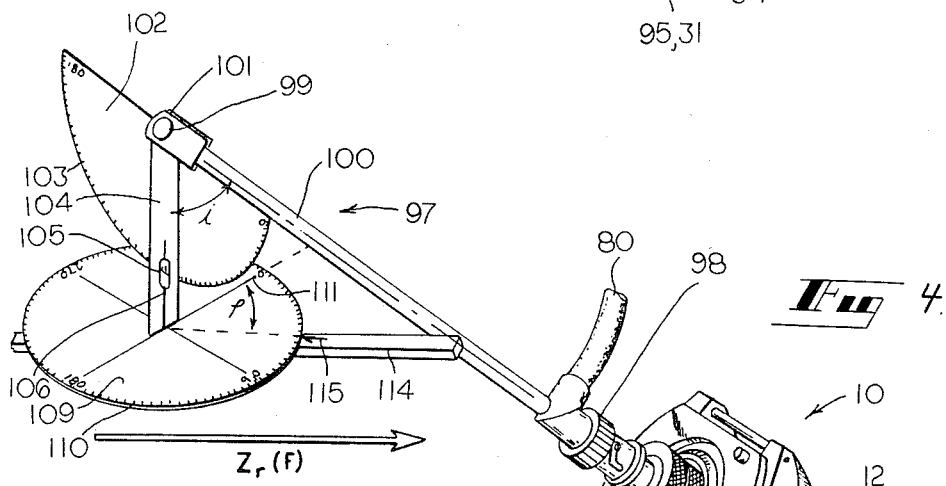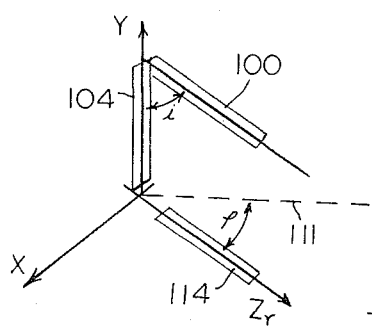

8,702

ULTRASONIC TESTING SYSTEM WITH VARIABLE ANGLE TRANSDUCER MOUNT

FIELD OF THE INVENTION

This invention relates generally to the field of ultrasonic testing, and more specifically to signal transmitting equipment and methods.

BACKGROUND OF THE INVENTION

When focusing signals in ultrasonic testing, it often becomes necessary to transmit the signal beam at an angle to the mounting surface. In the existing prior art, angle beam transducers are manufactured at fixed wedge angles. When a change in the angle of observation (or focal point) is required, the transducers must be detached from the fixed wedge angle and reattached to the desired, different wedge angle. Multiple wedge sets must always be on hand; and, even then, the wedge angles are limited by manufacturers to standard effective angles of, for example, 30, 45, 60, 70 and 90 degrees.

SUMMARY OF THE INVENTION

Briefly described, the present invention comprises an apparatus and method wherein a single transducer is mounted for rotational and angular movement within a housing to thus provide a range of varying wedge angles without exchanging wedge elements. The apparatus of the present invention, in the preferred embodiment, includes a transducer search unit mounted to a ball joint housed within a housing such that the search unit moves as the ball joint moves within the housing. The transmitter end of the search unit is immersed during operation, and throughout its range of movement, in a fluid occupied chamber bordered at one wall by a flexible membrane.

In one embodiment of the present invention, the apparatus includes an angle determining device for determining the relative angle of observation, within an x-y-z coordinate system of the transducer after the transducer has been moved about within the housing.

One embodiment of the present invention comprises the above defined apparatus associated with a fluid conduit and valve, for ultrasonic searching and locating of a valve element.

It is, therefore, an object of the present invention to provide a single transducer assembly which achieves a variety of observation angles.

Another object of the present invention is to provide a transducer assembly adjustable to achieve an infinite variety of observation angles within a given range of angles.

Yet another object of the present invention is to provide a variable angle transducer assembly with a method and apparatus for determining the relative observation angle of the transducer throughout its variable array of angles.

Still another object of the present invention is to provide a valve testing and locating apparatus and method which utilizes an adjustable angle transducer assembly to search for, detect and determine the location of a valve element.

Other objects, features and advantages of the present invention will become apparant upon reading and understanding this specification in conjunction with the accompanying drawings.

BRIEF DESCRIPTION OF THE DRAWINGS

FIG. 1 is an exploded view of a variable angle transducer mount in accordance with the present invention.

FIG. 2 is a partially cut-a-way side view of the mount in FIG. 1, cut along line 2—2 of FIG. 1.

FIG. 3 is a side view of the variable angle transducer mount of FIG. 1 strapped for use to a valve housing, in accordance with the present invention.

FIG. 4 is a pictorial view of the variable angle transducer mount of FIG. 1, fully assembled and outfitted with a pitch angle determining device, in accordance with the present invention.

FIG. 4A is an angular representation of the pitch angle determining device of FIG. 4 in an x-y-z coordinate system.

DETAILED DESCRIPTION OF THE PREFERRED EMBODIMENTS

Figures 5, 5A:
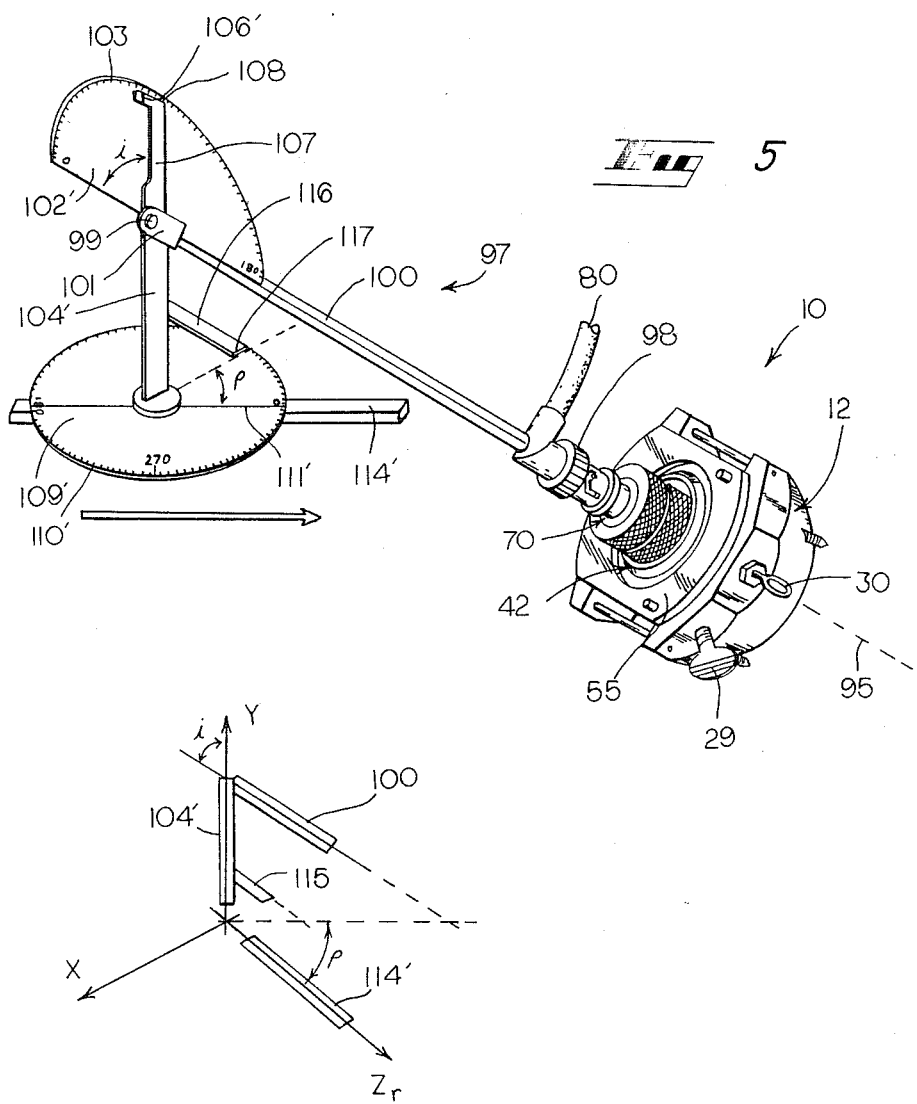
FIG. 5 is a pictorial view of the variable angle transducer mount of FIG. 1, fully assembled and outfitted with a pitch angle determining device of an alternate embodiment to that of FIG. 4.
FIG. 5A is an angular representation of the pitch angle determining device of FIG. 5 in a x-y-z coordinate system.

Referring now in greater detail to the drawings, in which like numerals represent like components throughout the several views, the present invention is seen as comprising a variable angle transducer mount 10 shown in exploded detail in FIG. 1. The transducer mount 10 comprises a housing 12 formed with a large cylindrical central channel 14, a flat top rim 15, flat bottom rim 16 and an outer wall 18. The outer wall 18 defines an upper segment which is wider in cross-section (see FIG. 2) than the bottom rim 16, and a tapered, lower segment 20. At the bottom rim 16, a circular ledge 25 is formed protruding into the central channel 14. Three, parallel, internally threaded bores 23 extend from the top rim 15, through the upper wall segment 19 and break the surface of the housing 12 through the tapered, lower segment 20. A threaded pin 24 occupies the bottom end of each of the bores 23, and protrudes from the tapered wall segment 20. The amount of protrusion of the pins 24 is adjustable by virtue of the threaded nature of the bores 23 and pins 24. Two strap holding pins 27 are mounted at the upper wall segment 19. The housing 12 is also formed with a threaded screw hole 28 extending generally perpendicular to the cylindrical axis 31 of the central channel 14, from the outer wall 18 through the upper segment 19 and into the central channel 14. A flat-end screw 29 occupies this screw hole 28 and is of sufficient length to extend from the outer wall 18 to the central channel 14. An eyelet 30 is bolted to the upper wall segment 19; but its bolt portion does not extend into the central channel 14.

A disk shaped membrane 34, of diameter greater than the inside diameter of the circular ledge 25 is placed in the central channel 14, resting on the circular ledge 25. A spacing washer 35 is set on top of the membrane 34 and is supported by the circular ledge 25, thus sandwiching the peripheral edge of the membrane between the washer and the circular ledge. A ball joint assembly 42 is set into the central channel 14 atop the washer 35. The ball joint assembly includes a rim segment 44 and a ball segment 45. The rim segment 44 includes a cylindrical outer wall 47 of diameter, preferrably, only slightly less than the inside diameter of the central channel 14.

The rim segment 44 also includes an inner passage 48 formed to accept the ball segment 45 in a manner typical to ball joint assemblies. The ball segment 45 is mounted in the inner passage 48 and enjoys complete rotational and pivotal freedom within the rim segment 44, as is typical of ball joint assemblies. The ball segment 45 is provided with a central, cylindrical passage 50 extending completely through the center of the ball segment. A threaded element 52 is press-fitted into the cylindrical passage 50 of the ball segment 45. A hole 46 is drilled through the rim segment 44 perpendicular to the cylindrical axis of the outer wall 47 and extending from the outer wall 47 through to the inner passage 48. The hole 46 is filled with a plug 49 which, preferably, extends the full length of the hole. In preferred embodiments, the plug is formed of brass. When the ball joint assembly 42 is set into the housing channel 14, the hole 46 of the rim segment 44 is aligned with the threaded screw hole 28 in the housing.

A clamp plate 55 is set on the top rim 15 of the housing 12. The clamp plate 55 is formed with a central opening 56. In the disclosd embodiment, the central opening 56 is circular, having an inside diameter which is less than the inside diameter of the central channel 14 of the housing 12. The inside diameter of the opening 56 is sufficiently large to avoid contact with the ball segment 45 as it pivots in the rim segment 44 of the ball joint assembly 42. The clamp plate 55 is held to the rim 15 of the housing 12 by screws 58 extending into the threaded bores 23 of the housing 12. As seen, the screws 58 occupy the same bores 23 as the threaded pins 24.

Once the above mentioned elements are all in place, it is seen that a chamber 62 is formed above the membrane 34. This chamber 62 is accessed through the passage 50 in the ball segment 45. A couplant material 63 is placed in the chamber 62 through the passage 50. In the preferred embodiment, the circular ledge 25, membrane 34, washer 35 and rim segment 44 of the ball joint assembly 42 define a combined height which is equal to or slightly greater than the full height of the housing channel 14. Thus, as the clamp plate 55 is screwed down onto the housing rim 15, it presses the rim segment 44, washer 35 and membrane 34, as a clamp, against the circular ledge 25; thereby creating a seal at the membrane 34 preventing leakage of the couplant 62. A transducer search unit 70 is held within the cylindrical passage 50 of the ball segment 45. The search unit 70 is of a type known in the industry, including an elongated, cylindrical body 71, a signal head 72 and a connector end 73. The otherwise typical search unit 70 is, for purposes of the present invention, formed with a threaded segment 74 along the head end of its body 71. A signal carrying cable 80 is connected by matching cable connector 81 to the search unit connector end 73. The cable 80 extends to the signal generating and recording unit 82 of a type known in the industry. The search unit 70 is held within the ball segment 45 by threading the threaded segment 74 of the search unit into the threaded element 52 of the ball passage 50. In the preferred embodiments, the search unit is seated far enough into the threaded element 52 and there is sufficient couplant material 63 within the chamber 62 such that the signal head 72 is, at all time, immersed in couplant material 63.

It can be seen that, as the ball segment 45 rotates and pivots within the rim segment 44, the search unit 70 rotates and pivots with the ball segment. Whereas, prior to seating of the search unit 70 in the ball segment 45, the ball segment enjoyed complete and unlimited rotational and pivotal movement within the rim segment 44, such unlimited movement is now restricted by the protruding search unit body 71. Nonetheless, the combination search unit 70 - ball segment 45 continues to enjoy complete 360° rotational freedom about the cylindrical axis 31 of the central channel 14 (as depicted by arrows "$\phi$"), and enjoys at least limited angular (pivotal) movement from the axis 31 (as depicted by arrows "$\alpha$"). See FIG. 2. It is noted that the washer 35 is of sufficiently large inside diameter to avoid possible binding of the ball segment 45 by the washer 35 as the ball segment rotates and pivots. Furthermore, in the preferred embodiment, the washer 35 is of sufficient height to act as a spacer between the membrane 34 and ball segment 45 which prevents striking of the membrane by the ball segment 45 or by the head 72 of the search unit 70 as the ball and search unit rotate and pivot.

FIG. 3 depicts the variable angle transducer mount 10 mounted for use, in one of its preferred applications, upon a valve body 85. In a more general sense, the valve body 85 will sometimes be referred to as the fluid conduit 85. In such an application, the transducer mount 10 is moved manually about the conduit 85 to a location which the user deems practical (based upon the contour of the valve body/conduit 85) for transmitting a signal to the generally anticipated location of a valve element 86 within the valve body 85. A couplant paste 89 is liberally smeared on the conduit 85 at the location where the transducer mount 10 is to be placed. The transducer mount 10 is placed against the conduit 85 with its membrane 34 being immersed in the coupling paste 89 and the bottom rim 16 and membrane 34 as close as practicable to the conduit surface - touching if possible. In the preferred embodiment, the membrane 34 is flexible and the membrane contacts the conduit 85 surface and takes on the contour of the conduit. The transducer housing 12 is held stationary on the conduit. The transducer housing 12 is held stationary connected to the strap holding pins 27 of the transducer housing 12 and encircling the valve body 85. Assisting in holding the transducer housing 12 in place are the threaded pins 24 which protrude from the lower wall segment 20 of the housing 12. These pins 24 are pointed at their ends and act as "contact feet" which assist in minimizing the skidding or sliding of the housing 12 along the conduit 85. It is noted that the pins 24 are adjustable and protrude only far enough to make contact with the conduit 85 without unnecessarily lifting the bottom rim 16 and membrane 34 away from the conduit surface. Also assisting in maintaining the housing 12 in place is a tie down string 92 which, as shown, is connected to the eyelet 30 and tied to an appropriate object to cooperate with the contact feet 24 in countering slippage and skidding of the housing along the conduit surface.

With the transducer housing 12 in place, the user begins sending an ultrasonic signal 94 (also referred to herein as a sound wave or signal beam) from the head 72 of the search unit 70. The transmission of signals is done in a manner known in the industry; and, in the preferred embodiments a "pitch and catch" technique is used in a manner known in the art to "view" the objects (i.e. valve elements 86) of the valve body 85. In search of the valve element 86 within the valve body 85, the user rotates and pivots the search unit 70 within the limits of the freedom of movement provided by the transducer mount 10 design as expressed above. The pivoting and rotating of the search unit 70 is accomplished without moving the housing 12 and signals 94 are sent from all the various positions of the search unit 70 and received and analyzed. Once the user has satisfied himself/herself that the object (i.e. valve 86) being sought has been located, or has otherwise satisfied himself/herself as to the search unit 70 position, the search unit is locked in that position. The position is locked by turning the flat-end screw 29 to screw it further into the screw hole 28 until the flat end of the screw contacts the plug 49 in the rim segment 44 of the ball joint assembly 42. Continued insertion of the screw 29 pushes the plug 49 along the hole 46 until it is pressed against the outer surface of the ball segment 45, thus binding the ball segment and preventing further movement. In the preferred embodiment, as mentioned above, the plug 49 is made of brass, in an effort to prevent its scratching of the highly polished surface of the ball segment 45.

The signal generating and recording unit 82 provides the electrical pulse required by the transducer search unit 70 and also collects and records new resultant, returned signals, converting them to time and distance values, all in a manner known in the industry. Thus, a distance value of the observed valve element 86 segment from the transducer head 72 is provided.

It can be seen that it is possible to determine the distance from the search unit head 72 of the segment of the valve element 86 being "looked at" by the search unit 70. This determination is made in accordance with principles of ultrasonic testing. It now becomes necessary to determine the direction of the observed segment of the valve element 86 from the search unit head 72, in order to accurately determine the location of a segment of the valve element. In order to establish the relative direction of the observed valve 86 segment from the search unit head 72, the preferred embodiment of the present invention determines the relative angle of the center line 95 of the signal beam 94 with respect to the x-y-z planes. The center line 95 of the signal beam will, also, be referred to herein as the "observation axis" 95. This relative angle of the observation axis 95 to the x-y-z planes shall be referred to as the "pitch angle".

In accordance with one, preferred embodiment of the present invention, the pitch angle is determined through use of a pitch angle device 97 as seen in FIG. 4. The pitch angle device 97 comprises a cable connector adaptor 98 which allows for access of the signal cable 80 at a right angle to the search connector end 73. (See FIG. 4.) Welded or otherwise attached to the connector adaptor 98 is a first post member 100. The first post member 100 is attached so as to extend parallel to the central axis of the search unit body 71 when the connector adaptor 98 is attached to the connector end 73 of the search unit 70. In the preferred embodiment disclosed hereby, the central axis of the search unit body 71 is colinear with the centerline 95 of the signal beam 94. The post member 100 is formed with a swivel joint 101 at its free end. Also mounted at the free end of the post member 100 is a first protractor device 102 which is semicircular in profile and includes angular indicia 103 along its outer edge in the manner of a typical protractor. The first protractor device 102 is fixedly mounted to the first post member 100. Connected to the swivel joint 100 and hanging from the first post member 100 is a second post member 104. This second post member 104 swivels freely within the swivel joint 101 and, thus, acts like a "plum line" in that it always seeks a vertical orientation. A thumb screw 99 at the swivel joint 101 is used to lock the relative movement between the first post member 100 and the second post member 104 once the vertical orientation of post 104 has been achieved. The second post member 104 is formed with a sight hole 105 from which the indicia 103 of the first protractor device 102 can be viewed. The sight hole 105 includes centerline markings 106 which represent the centerline of the post member 104 and, thus, the vertical axis. Fixedly attached to the lower end of the second post member 104 is a second protractor device 109 which is generally disk shaped. This second protractor device 109 defines a plane which is, in the preferred embodiment, perdendicular to the centerline of the second post member 104. The second protractor device 109 includes angular indicia 110 along its outer edge in the manner of a typical protractor. The diameter 111 which includes the reference (or zero degree) point is seen as being permanently oriented within the same plane as in the centerline 95 of the first post member 100, and thus the centerline of the observation axis 95. A third post member 114 (also referred to as the pivot post 114) is pivotally connected to the bottom of the disk protractor 109. The pivot post 114 is connected at the center point of the disk protractor 109 in order that it may pivot 360° about the centerline 106 of the second post member 104. During use, the pivot post 114 is used to represent a selected horizontal axis (Z axis). A centerline indicator mark 115 on the pivot post 114 represents the centerline of that post. A second thumb screw (not seen) at the connection between the pivot post 114 and the second post member 104 locks the pivot post relative to the second post member when desired.

Thus, in operation, it can be seen that the pitch angle device 97 is utilized to establish the pitch angle of the observation axis 95 as follows: the first post member 100 is attached to the transducer search unit body 71 and, thus, represents the observation axis 95; the angle of the observation axis 95 with respect to the vertical axis (Y axis) 106 is read at the sight hole 105 from the first protractor device 102 and is called the "inclination angle ($\lambda$); the pivot post 114 is pivoted to align parallel with a chosen horizontal axis (Z axis), also called the reference Z axis ($Z_r$) - for example, in the disclosed valve element detecting application of FIG. 3, the reference Z axis lies within a vertical plane parallel to the direction of fluid flow "F"; the angle of the observation axis 95 with respect to the chosen Z axis is read from the disk protractor 109 at the pivot post indicator mark 115 and this angle is referred to as the "plane angle" ($\rho$); and, finally, the pitch angle (PA) is calculated by the following formula:

$$PA = INVTAN (COS\rho - TAN\lambda)$$

After having acquired the distance value utilizing the ultrasonic transducer and the pitch angle using the pitch angle device, the user is now able to locate the observed segment of the valve element 86 (or other observed object). By now loosening the flat-end screw 29 to again free the ball segment 45 for movement, the user pivots and rotates the transducer search unit 70 to observe yet another segment of the valve element 86. By repeating the steps mentioned above, the user can establish a distance and pitch angle for numerous segments of the valve element 86, thus creating a trace of the valve element 86 to accurately establish the orientation and position of the valve within the valve body 85. These distance and angle measurements can be translated to two and three dimensional drawings in order to give interested parties a "picture" of the valve element 86 within the valve body 85. It is understood that there is the possibility of circumstances where the fluid conduit 85 will itself be tilted so that the direction of fluid flow "F" is not within a horizontal plane. In such a situation, transferring of pitch angle measurements to a two or three dimensional drawing will be facilated by modifying the pitch angle to compensate for the tilt of the valve body 85. This is accomplished by acquiring a reading of the inclination angle of the valve body 85; that is, the angle of inclination of the fluid flow "F" with respect to the veritcal axis (Y axis) is determined and substracted from the angle of inclination first established above and substituting this remainder as the angle of inclination in the above mentioned equation for pitch angle.

An alternate embodiment of the pitch angle device 97 is seen in FIG. 5. In this alternate embodiment, the first protractor device 102′ is fixedly mounted to the top edge of the first post member 100. The second post member 104′ includes an extension arm 107 which is a part of and moves with the second post member 104′. The extension arm reaches the indicia 103′ of the first protractor device 102′ where its head end 108 bears a centerline marking 106′ which represents the centerline of the post member 104′ and, thus, the vertical axis. The second protractor device 109′, of the embodiment of FIG. 5, is pivotally connected to the bottom of the second post member 104′. This disc protractor 109′ is connected with its centerpoint at the centerline of the second post member 104′ in order that the disc 109′ rotates 360° about the centerline of the second post member 104′. The third post member 114′ is, in this embodiment, fixedly attached to the disc protractor 109′ with the centerline of the third post member lying parallel to and coplaner with the reference diameter 111′ of the disc protractor. A leg 116 is fixedly attached to the second post member 104′ and defines a pointer 117 at its free end. The leg 116 is of such length and orientation that the pointer 117 is located slightly above the disc protractor 109′ and adjacent the indicia 110′ of the disc. The pointer 117 is permanently positioned within the same plane as the centerline 95 of the first post member 100, and thus the centerline of the observation axis 95. The pitch angle device of FIG. 5 functions similarly to that of FIG. 4. However, in this embodiment, as the pivot post 114′ is pivoted to align with the reference Z axis, the disc protractor also pivots (rotates). Thus, the plane angle ($p$) is read at the leg pointer 117. The inclination angle ($i$) is read at the centerline marking 106′ on the extension head 108.

In alternate embodiments of the present invention wherein the variable angle transducer mount 10 is to be utilized in high temperature environments, a lubricant comprising graphite occupies the joint between the ball segment 45 and rim segment 44 of the ball joint segment 42. In preferred embodiments of the present invention, the couplant material 63 is a fluid couplant, chosen from existing couplants, which has a boiling point exceeding the maximum operating temperature, maintains a relatively stable volume over the operating temperature range, is a good transmitter of sound, is non-destructive to the exposed transducer head 72 and is of sufficiently high viscosity to prevent leakage through the ball joint assembly 42. The membrane 34 of preferred embodiments is characterized in that it has low attenuation properties, withstands temperatures within the operating temperature range, has sufficiently low porosity to prevent leakage or passage of the couplant material, and does not react with the couplant material 63 or the couplant paste 89. An example of such membrane is a silicone rubber of, for example, 0.030 inch thickness.

In alternate embodiments of the present invention, the clamp plate 55 provides an additional function as a template. That is, the central opening 56 of the clamp plate 55 is varied in shape and diameter to define an outer range of pivotal movement (i.e. angle "$a$"). The thickness of the clamp plate 55 at the location of the central opening 56 is also varied to assist in this template function. Without limiting the purpose of this template, it can be seen that the template is used to prevent the observation axis 95 from striking the surface of the valve housing 85 at an angle which exceeds the allowable critical angle for the particular metal from which the conduit 85 is fabricated.

In an alternate embodiment of the transducer mount 10 of the present invention, the membrane 34 is not present. In this embodiment, the spacing washer 35 is retained to maintain the ball joint assembly 42 a selected distance away from the bottom rim 16 of the housing 12. In this way, as the rim 16 is placed in contact with the valve body 85 or other casing, the ball segment 45 and transducer head 72 will not strike the valve body as the ball segment and transducer search unit 70 are rotated and pivoted within the housing 12. In this alternate embodiment, the user must be carefull to maintain a continuous supply of couplant paste and/or fluid or other couplant material between the transducer head 72 and the valve body 85 in order that the ultrasonic sound signal 94 is not transmitted through air.

It is understood that the valve housing application of FIG. 1 is only one application of the apparatus and method of the present invention. The present invention is not to be limited by the specifics of the disclosed application. Rather, the valve body/conduit 85 and valve 86 are representative of casings and observed objects, respectfully, encountered in other applications.

Furthermore, whereas the present invention has been described in detail with specific reference to preferred embodiments and applications thereof, it will be understood that variations and modifications can be effected within the spirit and scope of the invention as described before and as defined in the appended claims.

We claim:

1. Method of searching for, detecting and locating a valve element within a fluid conduit, said method comprising the steps of:

mounting a transducer search unit for rotational and angular movement within a housing;

immersing the transmitter head of the search unit in a fluid couplant within the housing;

holding the housing stationary against the fluid conduit;

repeatedly transmitting a signal beam from the search unit into the conduit in search of the valve element and receiving the reflected beam;

rotating and pivoting the search unit within the housing while repeatedly transmitting the signal beam;

detecting the valve element with the signal beam;

measuring the inclination angle between the centerline of the signal beam and the vertical axis;

measuring the plane angle between the centerline of the signal beam and the direction of fluid flow through the conduit at the valve; and calculating the location of the valve element relative to the transmitter head.

2. Method of claim 1, wherein the step of calculating the location of the valve element relative to the transmitter head comprises the steps of:
- determining the distance traveled by the signal beam from the transmitter head to the valve element;
- calculating the pitch angle of the centerline of the signal beam utilizing the formula: Pitch angle equals the inverse tangent of the difference of the cosine of the plane angle minus the tangent of the inclination angle; and
- establishing the location of the valve element at the determined distance from the transmitter head along the calculated pitch angle.

3. Method of searching for, detecting and locating an object within a casing, said method comprising the steps of:
- mounting a transducer search unit for rotational and angular movement within a housing;
- immersing the transmitter head of the search unit in a fluid couplant;
- holding the housing stationary against the casing;
- repeatedly transmitting a signal beam from the search unit into the casing in search of the object and receiving the reflected beam;
- rotating and pivoting the search unit within the housing while repeatedly transmitting the signal beam;
- detecting at least a segment of the object with the signal beam;
- measuring the inclination angle between the centerline of the signal beam and the vertical axis;
- measuring the plane angle between the centerline of the signal beam and a reference Z-axis; and
- calculating the location of the segment of the object relative to the transmitter head.

4. Method of claim 3, wherein the step of calculating the location of the segment of the object relative to the transmitter head comprises the steps of:
- determining the distance traveled by the signal beam from the transmitter head to the object segment;
- calculating the pitch angle of the centerline of the signal beam utilizing the formula: Pitch angle equals the inverse tangent of the difference of the cosine of the plane angle minus the tangent of the inclination angle; and
- establishing the location of the object segment at the determined distance from the transmitter head along the calculated pitch angle.

5. Method of claim 4, further comprising the step of maintaining the housing stationary against the casing while repeating a plurality of times in sequence the steps of rotating and pivoting the search unit within the housing while repeatedly transmitting the signal beam, detecting a segment of the object with the signal beam, measuring the inclination angle, measuring the plane angle, and calculating the location of the detected object segment relative to the transmitter head to trace at least a large portion of the object.

6. Method of claim 5, further comprising the step of providing a representative drawing depicting the relative positions of the traced portion of the object, the casing and the transducer head.

* * * * *